Figure 1:
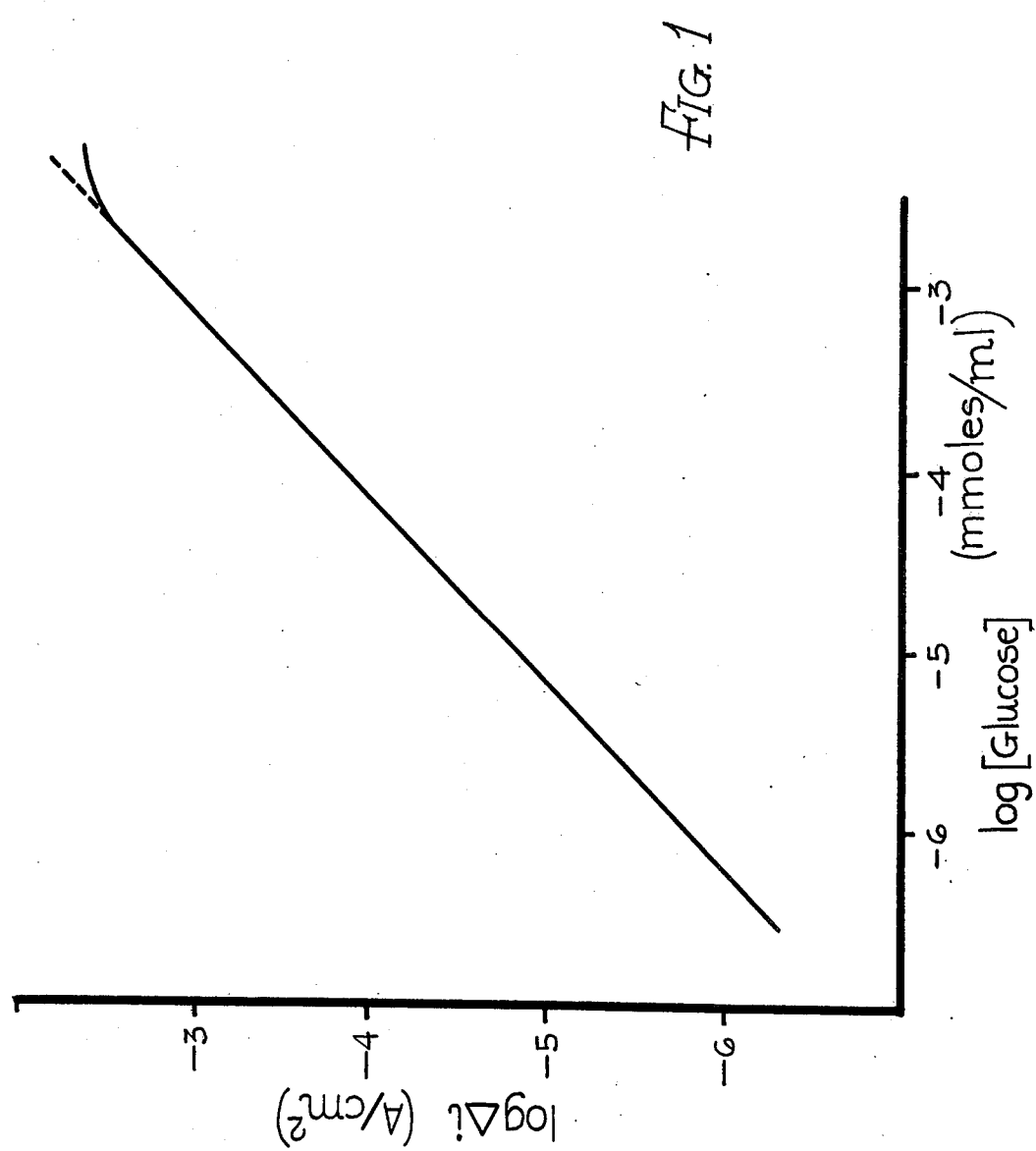

United States Patent [19]

Schick et al.

[11] 4,127,448

[45] Nov. 28, 1978

[54] AMPEROMETRIC-NON-ENZYMATIC METHOD OF DETERMINING SUGARS AND OTHER POLYHYDROXY COMPOUNDS

[76] Inventors: Karl G. Schick, 5050 N. 19th St., Milwaukee, Wis. 53209; Calvin O. Huber, 707 W. Pioneer Rd., Mequon, Wis. 53092

[21] Appl. No.: 772,454

[22] Filed: Feb. 28, 1977

[51] Int. Cl.² .............................................. G01N 27/46
[52] U.S. Cl. ...................................... 204/1 T; 204/96
[58] Field of Search ........................ 284/1 TK, 195 R

[56] References Cited

U.S. PATENT DOCUMENTS

| | | | |
|---|---|---|---|
| 3,141,835 | 7/1964 | Rolin et al. | 204/195 R |
| 3,539,455 | 11/1970 | Clark | 204/1 P |
| 3,948,745 | 4/1976 | Guilbault et al. | 204/195 B |
| 3,979,274 | 9/1976 | Newman | 204/195 B |

*Primary Examiner*—T. Tung
*Attorney, Agent, or Firm*—McDougall, Hersh & Scott

[57] ABSTRACT

A method for determining hydrogen peroxide, sugars and other polyhydroxy compounds in blood serum, urine and aqueous solutions by direct electrochemical oxidation in aqueous alkaline medium with a transition metal oxide catalyst electrode in the presence of lithium hydroxide in solution.

15 Claims, 3 Drawing Figures

AMPEROMETRIC-NON-ENZYMATIC METHOD OF DETERMINING SUGARS AND OTHER POLYHYDROXY COMPOUNDS

This invention relates to a direct electrochemical method for determining the presence and amount of hydrogen peroxide and organic polyhydroxy compounds including organic compounds that yield polyhydroxy compounds.

Representative of the organic polyhydroxy compounds that are capable of direct electrochemical determination by the method of this invention are the diols, triols and other polyols including sugars such as the disaccharides, maltose and lactorse, and non-reducing sugars such as sucrose, hydrogen peroxide, serum glucose, serum triglyceride, cholesterol, cholesterol esters and the like.

Considerable attention has been addressed recently to the need for a simple, efficient, and effective means for the determination of sugar in blood or urine and the invention will therefore be described hereinafter with particular reference to its application in the direct electrochemical analysis for glucose sugar.

The need for speed and precision in the determination of glucose has led to the development of numerous methods and procedures (1, 2). Enzymatic techniques have been utilized in order to increase the specificity of the glucose assay. Such enzymatic methods frequently involve the coupled glucose oxidase-peroxidase enzyme system. These procedures involve indirect methods of analysis that are slow, time consuming, difficult and expensive.

(1) Cooper, G. R., CRC Crit. Rev. in Clin. Lab. Sci., 101 (1973) (2) Haltman, Clinical Biochemistry: Principle and Methods, H. C. Curtius (Ed.), Malter DeGruyter, New York, 1974, p. 909.

The use of electrochemical techniques for enzymatic determination of glucose has received much attention in recent years. Several potentiometric methods have been devised. Other electrochemical techniques include constant current as well as constant potential monitoring of hydrogen peroxide generated in the enzymatic oxidation of glucose. Some methods utilize electron-acceptors which react with the hydrogen peroxide. Other techniques involve the monitoring of oxygen-uptake during the enzymatic oxidation process by means of an oxygen electrode. All of the electrochemical assay techniques that have been developed for the determination of blood glucose have been indirect and are therefore subject to numerous interfering side reactions.

It is an object of this invention to provide a direct electrochemical analysis for glucose and other dihydroxy, trihydroxy and polyhydroxy compounds or compounds that can be reacted to yield such hydroxy compounds, in which the measurement can be made without interfering side reactions such as normally experienced with indirect measurements of the types heretofore employed, in which the analysis can be carried out by means of stable components which enable reproducible results with minimum deviation, in which the process can be carried out without the need for making use of techniques for immobilization of enzymes, in which only a minimal amount of test material is required for the determination, and in which the process of analysis can be reduced to a unit operation for rapid and inexpensive assay.

Figure 2:
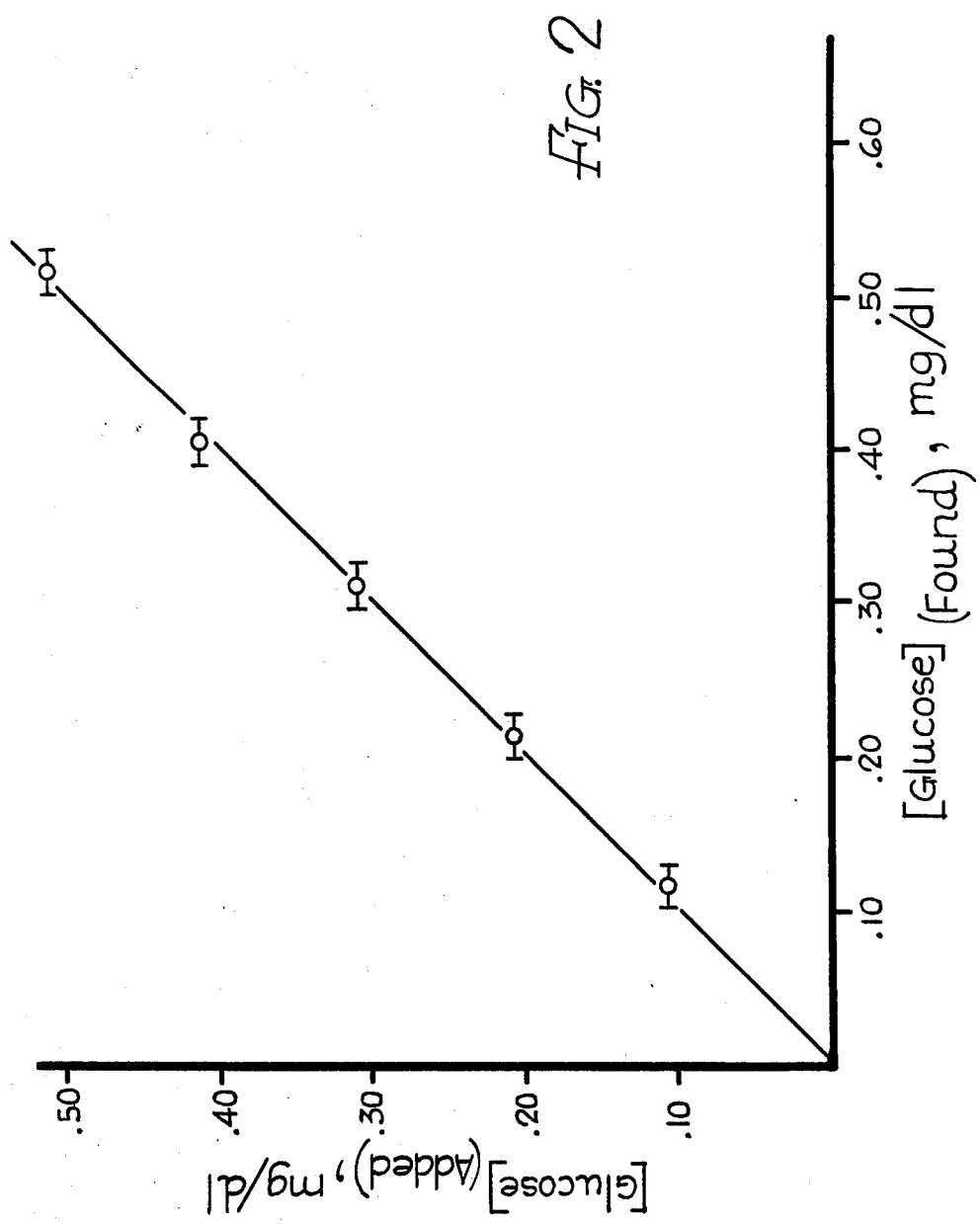
Figure 3:
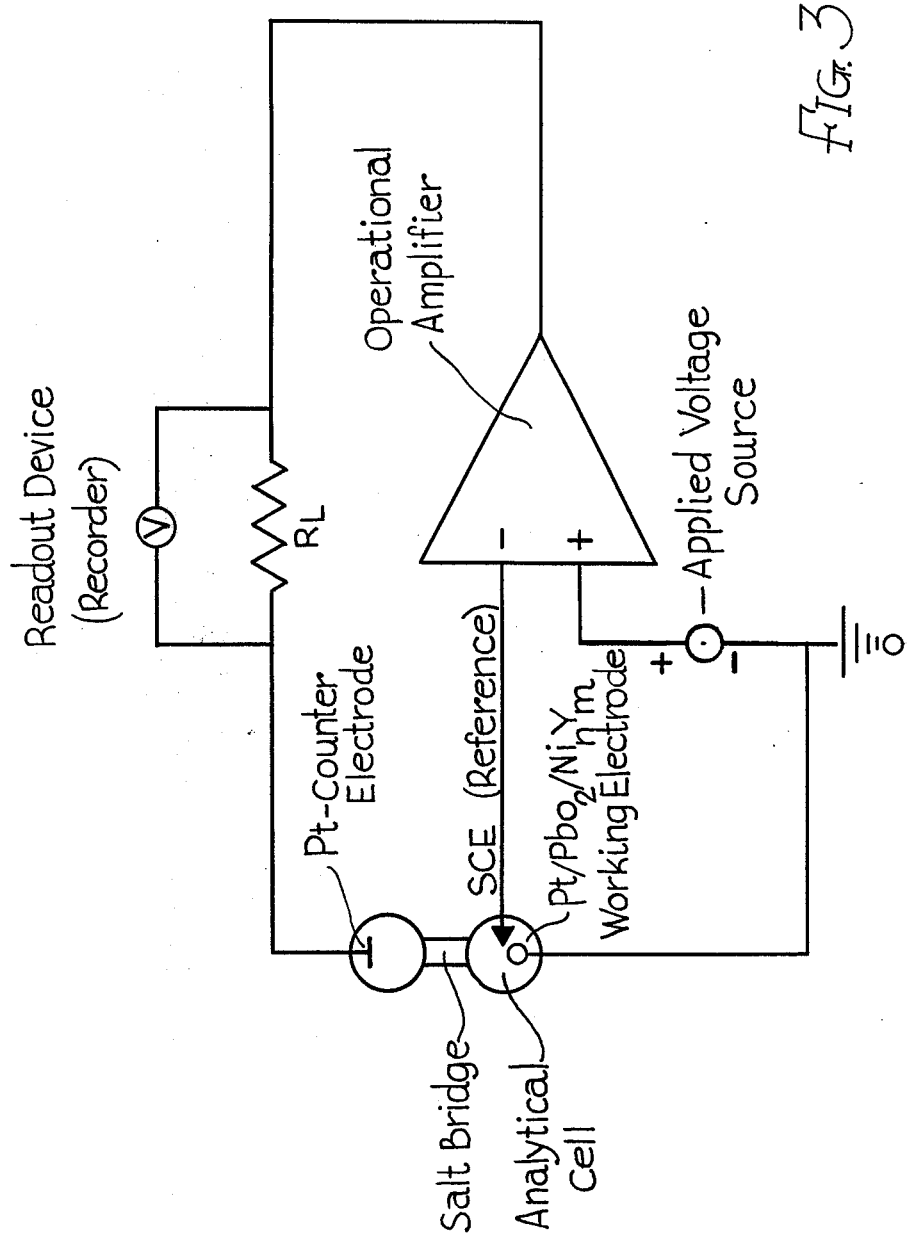

These and other objects and advantages of this invention will hereinafter appear and for purposes of illustration, but not of limitation, an embodiment of the invention is shown in the accompanying drawings in which FIG. 1 is a graph showing analytical current response in glucose concentrations within the range of $5 \times 10^{-7}$ to $1 \times 10^{-3}$;

FIG. 2 is a correlation diagram between calculated and determined amounts of glucose; and FIG. 3 is a diagrammatic sketch of the apparatus employed in the determinations of this invention.

The method of this invention is based upon the direct, electrochemical oxidation of sugars and other polyhydroxy compounds in alkaline medium, preferably containing transition metal ions. The oxidation is accomplished by means of a stable, catalyst which is electrodeposited on a conductive metal oxide electrode surface and in which the oxidation is carried out at an applied electrodepotential.

Briefly described, the method of this invention concerns the direct electrochemical oxidation of hydroxy compounds in the presence of a transition metal oxide catalyst electrode in which the polyhydroxy compound is dissolved in aqueous medium at high pH derived from the presence of lithium hydroxide and which may contain in solution ions of the metal of the metal oxide catalyst.

The following will illustrate the practice of this invention in the determination of glucose in blood serum by direct electrochemical oxidation with a stable nickel oxide catalyst.

EXAMPLE 1

Apparatus:

A potentiostat/galvnostat (Princeton Applied Research, Mode 723) was used for all of the electrochemical measurements. For measuring currents, the output of the current-voltage converter was monitored with a Sargent Recorder (Model MR). A three-electrode system, consisting of working electrode (Pt/PbO$_2$/Ni$_n$O$_m$), platinum counter electrode, and a commercial saturated calomel reference electrode was used. The sample container was a 50 ml beaker with magnetic stirrer. The counter electrode was separated from the working and reference electrode in the sample container by means of a salt bridge containing 0.10 M LiOH solution in water, with fritted glass ends. Analytical measurements were carried out at an applied potential of +500 mV vs S.C.E.

Preparation of electrode:

An electrode consisting of a planar, disc platinum (or gold) electrode is immersed into a plating solution that is made up of 2.0 M LiOH, 0.2 M PbO and 0.2 M NiSO$_4$. A small sheet (1.5 cm $\times$ 10.0 cm) of lead metal is used as a cathode. A plating current of $5 \times 10^{-3}$ A/cm$^2$ is applied for 30 minutes. The anode is removed from the plating bath and thoroughly rinsed with distilled water. The dark gray surface of the electrode consists of a mixture of lead dioxide and nickel oxides. The presence of nickel oxide catalyst on the electrode surface is determined quantitatively by cyclic voltammetry in a 0.1 M LiOH solution. At a scan rate of $10^{-2}$ cycles/sec, two characteristic peaks are observed as the nickel oxide catalyst, an anode peak at ~ 405 mV (SCE) and a cathode peak at ~ 3 15 mV (SCE).

In an alternative method for preparation of the electrode, a planar disc platinum (or gold) electrode is electrodeposited with PbO$_2$. The electroplating is carried out in a stirred 2.0 M NaOH solution saturated with PbO. The platinum electrode serves as the anode. A small sheet of lead metal is used as a cathode. A current density of $4 \times 10^{-4}$ A/cm$^2$ is applied for 2 hours. The nickel oxide catalyst is then electrodeposited on the PbO$_2$ electrode surface by immersing the electrode into a fresh solution consisting of 0.1 M LiOH, 0.01 M NiSO$_4$ and 0.01 M glucose. A different platinum electrode serves as a cathode. A current density of $5 \times 10^{-3}$ A/cm$^2$ is applied for 20 minutes. After thorough rinsing of the nickel catalyst electrode is distilled water, the presence of absorbed nickel catalyst is evaluated qualitatively as well as quantitatively in a 0.1 M LiOH solution by cyclic voltammetry.

The redox catalyst is immobilized via electrodeposition in the second method or co-electrodeposition in the first method. In both cases, the matrix upon which the catalyst is deposited consists of conductive PbO$_2$ in place of which any other conductive, insoluble metal oxide can be used, and which has a large specific surface area. This large surface area of the metal oxide allows the loading of the electrode surface with catalyst. Thus the high catalyst surface concentration gives rise to large current density during serum glucose oxidation.

For the blood serum glucose determination, a wet 0.4µ Nuclepore filter (Nuclepore Corporation) was press-fitted over the surface of the catalyst electrode and secured with an O-ring. This measure was employed in order to prevent electrode surface adsorption of blood serum proteins.

Reagents and Samples:

The reagent solutions were prepared using a distilled-deionized water and the materials were of reagent grade.

Lab Trol (Dade, Lot No. LT-4SEK) and Patho-Trol (Dade, Lot No. PT-718) solutions were used as blood serum standards.

Fresh blood serum samples were obtained from nearby hospital. Twenty-three samples with serum glucose concentrations ranging from 30 to 430 mg/dl were used.

Procedure:

While applying a constant potential of +500 mV (S.C.E.), the nickel catalyst electrode was equilibrated in 25.0 ml of 0.10 M aqueous solution of LiOH containing 1 mM NiSO$_4$ (pH 13) until a constant base line current was obtained (about 2 minutes). In separate tests, sample and standards were added to the solution with a 50 µl syringe. The changes in current arising from the additions were recorded. The current changes resulting from the oxidation of the added glucose is referred to as the analytical current, $\Delta i$. A stable value was achieved within 10 seconds. All measurements were carried out at room temperature using a fixed-setting, temperature equilibrated magnetic stirrer.

In the presence of NiSO$_4$ in solution, the analytical current response ($\Delta i$) is linear in the glucose concentration range from $5 \times 10^{-7}$ M to $1 \times 10^{-3}$ M (FIG. 1). Linear calibration plots were also obtained for commercial control serum at pH 13 (0.10 M LiOH) containing 1 mM NiSO$_4$ (FIG. 2). The vertical axis represents the calculated glucose concentrations of the diluted control serum samples. These concentrations were calculated from the stated glucose concentrations of the commercial control serum (261 mg/dl). The horizontal axis represents those glucose concentrations which were obtained by comparing the control serum analytical currents with those measured for glucose standards. Each data point of the correlation diagram represents the mean of five measurements.

Serum glucose determinations on real samples were carried out using the commercial Patho-Trol control serum as a standard. The glucose analytical current arising from the control serum additions were compared to those resulting from blood serum additions. At least five alternating additions of 25 µl of standard Patho-Trol and 25 µl of blood serum were made for a given sample. The blood serum samples had been previously analyzed independently by the hospital laboratory, using the hexokinase method. The deviation if any between the results obtained were relatively negligible (corr. coef., 0.998).

The typical blood serum size was 25 µl. However, samples as small as 5 µl have successfully been analyzed. Twenty repetitve analyses of one sample yielded a coefficient of variation of less than 4%.

Interference studies in alkaline solution containing 1 mM of NiSO$_4$ indicate that ascorbic acid is rapidly decomposed and thus has no effect upon the analytical signal for glucose. Uric acid does not interfere at the concentration found in blood serum. Chloride ions, which have been reported to interfere with glucose oxidation in neutral solutions, do not interfere under the conditions described. Zinc hydroxide, which is frequently used as a deprotenizing agent, acts as a strong catalyst poison, inhibiting the electrode response to glucose. However, deproteinization of samples is not required by the method of this invention with the result that zinc hydroxide is not a factor. The presence of serum protein has no effect upon the serum glucose response when the electrode surface is covered with a membrane filter to prevent electrode surface adsorption of the protein.

When stored in air, the electrode surface remains active without further precautions or treatment for at least several weeks. Quantitative reproducibility of the glucose response was observed over a period of at least two weeks.

The described non-enzymatic method of this invention for determination of blood glucose has many advantages over presently available procedures. Direct measurement of glucose avoids interfering side reactions typically associated with indirect measurements. The electrochemical oxidation is accomplished by means of a stable, inorganic catalyst. The catalyst is readily immobilized via electrodeposition onto a conductive metal oxide surface. This procedure avoids the many difficulties encountered with some of the enzyme immobilization techniques employed in other electrochemical methods. The method of this invention requires minimal solution handling. Depending upon sample size, 20 to 30 successive standard or sample additions can be made to the same solution. Each addition of standard or sample yields a steady-state analytical current within 10 seconds. Since, in the procedure the sample is diluted about 1000 fold, very low or very high glucose samples can readily be accommodated by appropriate modification of the dilution. The method appears tobe readily amenable to automation. The specificity, sensitivity, and simplicity of the described direct electrochemical oxidation determination of polyhydroxy compounds indicates that a new and desirable procedure has been made available for determination of serum glucose and other sugars, polyhydroxy compounds and other compounds yielding polyhydroxy compounds.

Besides glucose, glycerol and other polyhydroxy compounds can be readily oxidized amperometrically at transition metal electrodes. Aromatic, di- or polyhydroxy compounds as well as hydrogen peroxide exhibit high rates of oxidation at such electrodes. For example, linear calibration plots have been obtained for glycerol, uric acid, and hydrogen peroxide in the $1 \times 10^{-7}$ to $1 \times 10^{-2}$ molar range. Thus, direct electrochemical oxidation can be used in accordance with the practice of this invention in determination of triglyceride and cholesterol.

For the determination of triglycerides and cholesterol in blood serum, it is desirable first to determine the amount of serum glucose, as in the manner described in Example 1. Thereafter, a portion of the serum is hydrolyzed enzymatically to convert the triglyceride to glycerol and fatty acid. Thereafter the glycerol can be electrochemically oxidized for determination in accordance with the practice of this invention, as will hereinafter be described.

For cholesterol determinations, the blood serum sample is reacted with cholesterol ester hydrolase and cholesterol oxidase. The first enzyme hydrolyzes the cholesterol esters to free cholesterol. The second enzyme oxidizes the free cholesterol in the serum plus the free cholesterol yielded upon hydrolyzation of the ester to produce hydrogen peroxide. The latter is then oxidized electrochemically in accordance with the practice of the invention for determination, as will hereinafter be described.

EXAMPLE 2

This example illustrates the method of this invention as applied to the determination of triglyceride in blood serum by hydrolysis of the serum triglyceride to fatty acids and glycerol, the latter representing the component on which the direct electrochemical analysis is performed to determine the amount of triglyceride in the serum.

0.25 ml of blood serum sample is diluted with 0.1 M phosphate buffer (pH 7) to 0.5 ml. The buffer contains 400 units of lipase (R. Delemar), 30 units of α-chymotrypsin and 10 mg bovine albumin. The solution was incubated for at least 10 minutes at 35° C.

In the presence of lipase and α-chymotrypsin, serum triglycerides are hydrolyzed to glycerol and fatty acids. The glycerol is then subjected to electrochemical oxidation in accordance with the procedure applied in Example 1 for the determination of glucose. For this purpose, 50 μl of the above solution were added to 25.0 ml of 0.10 M LiOH (pH 13.0) containing 1 nM NiSO$_4$.

The increase in current due to the addition of the above solution has two contributions, namely i(Total) = i(Gluclose) + i(Glycerol).

Having previously determined the contribution to the total current made by the presence of glucose in the serum sample, the current increase due to glycerol was readily determined via comparison with a standard glycerol addition (100 mg/dl).

A real blood sample obtained from a nearby hospital was analyzed for triglyceride in the manner described in Example 2. The results obtained indicated a triglyceride level of 530 mg/dl. This compared to the value of 535 mg/dl obtained by the standard spectrophotographic method of analysis.

EXAMPLE 3

This example illustrates the practice of this invention as employed in the determination of cholesterol in blood serum by direct electrochemical oxidation of hydrogen peroxide yielded by reaction of the cholesterol compound.

0.25 ml of blood serum sample was diluted to 0.5 ml with 0.1 M phosphate buffer (pH 7.0) containing 5 units/ml of cholesterol oxidase and 5 units/ml (or less) of cholesterol ester hydrolase. The solution was incubated in a 35° C. water bath for at least 10 minutes.

Blood serum contains two species of cholesterol, namely, free cholesterol and cholesterol ester. The cholesterol ester is enzymatically hydrolyzed during incubation to free cholesterol by means of the cholesterol ester hydrolase. The free cholesterol is then enzymatically oxidized by means of cholesterol oxidase to yield hydrogen peroxide which can be determined in accordance with the practice of this invention by direct electrochemical oxidation.

50 μl of the above incubated solution was added to 25.0 ml of 0.10 M LiOH (pH 13) in aqueous medium, containing 1 mM NiSO$_4$. The increase in current resulting from the addition of the solution has two contributions, namely, i Total = i Glucose + i Hydrogen peroxide.

Knowing the contribution made by glucose in the serum from previous analysis, the current increase due to hydrogen peroxide can be determined via comparison with a standard hydrogen peroxide aqueous solution (0.01 M).

Real blood samples obtained from a nearby hospital were analyzed for cholesterol in accordance with Example 3. The results obtained indicated a cholesterol level of 240mg/dl. The results obtained with the standard spectrophotometric test was 250 mg/dl.

In both examples 2 and 3, the electrode surface immersed in the solution was covered with 0.4μ Nuclopore filter to prevent surface adsorption or interference with the test by macromolecules present in blood serum.

While it is desirable to protect the working electrode from interference by proteins or other large or interfering molecules in determinations made on blood serum and other body fluids, such protective covers of microporous filters is not necessary when determinations by electrochemical oxidation are carried out on polyhydroxy compounds where such interfering molecules are not present, such as in the determination from aqueous solution of di-, tri- or polyhydroxy compounds. When employed to protect the electrode from protein or other large interfering molecules, use should be made of a membrane having small pores of 0.4μ or less, preferably tightly wrapped to enclose the electrode.

The nickel sulphate, employed in Examples 1 to 3, can be replaced by other sources of nickel ions such as other soluble nickel salts. The purpose is to make ions available in low concentration in the test solutions to regenerate the electrode. Thus when the electrode is formed of other transition metal oxides, such as of lead, manganese, rubidium, copper, nickel, cobalt or silver oxides, the free ions provided in the solution should correspond to the metal of the catalyst. While the useful life of the electrode is greatly prolonged and improved stabilization can be obtained by the presence of such metal ions in solution, such metal ions are non-essential in the direct analysis by electrochemical oxidation in accordance with the practice of this invention.

Determinations in accordance with the practice of this invention by electrochemical oxidation are strongly pH dependent. The determination cannot be carried out at a desirable rate at a pH as low as 7 while a pH in excess of 14 is impractical because of the corrosiveness of the solution. Within the above range, it is preferred to operate within a pH range of 10 to 14 with best results, from the standpoint of speed and accuracy, being obtained by the use of solutions wherein the pH is within the range of 11 to 13.

It is preferred to make use of lithium hydroxide for obtaining the desired pH since, with both sodium and potassium hydroxide, oxidation of water will occur at low potential, resulting in the interference with oxidation of the compound to be measured.

The presence of lithium hydroxide results in increase in oxygen over-potential at metal oxide electrode with corresponding increase in the useful potential range of the metal oxide electrode; formation of lithinated surface metal oxides of low solubility with corresponding increase in the lifetime of the electrode; and increase in conductance of surface metal oxides. It is believed that this results in part from the fact that lithium salts form at the surface of the electrode and become incorporated or absorbed as lithium ions in the matrix of the metal oxide to provide increased activity of the electrode. It is preferred to make use of lithium hydroxide in solution within the range of 0.1 to 1 M but the range is not critical in that use can be made in concentrations as low as 1 mM, depending somewhat upon the pH of the solution.

The lower detection limit for sugar and other polyhydroxy compounds lies in the sub-micromolar range. Linear calibration plots for these compounds have been obtained in the $1 \times 10^{-7}$ to $1 \times 10^{-2}$ molar range. When present in concentrations greater than the above, the response is non-linear. Thus samples should be diluted or concentrated to the desired range for analysis, as the case may be.

The determinations can be carried out at room temperature or slightly above or below room temperature since the reactions are not temperature dependent.

The presence of carboxyl groups in the compound to be tested does not interfere with the electrochemical oxidation reaction. Thus the invention can be employed for the determination of sugar present in urine. The enzymatic reaction product of uric acid gives rise to an electrochemically inert product that enables the determination of glucose sugar in urine.

However, as in the determination of triglycerides or cholesterol in blood serum, determination is first made electrochemically for urine. The urine is reacted enzymatically with uricase and urease. The difference in electrochemical oxidation values between the value for the urine and the value for the enzymatically reacted product is the result of the inactivation of the uric acid by decomposition to allantoin. The remaining signal is due to the presence of glucose sugar and thus gives a measurement of the amount of sugar in the urine.

Correlation of better than 0.998 has been observed by the determination of glucose in serum or urine in accordance with the practice of this invention as compared with the determination of the same materials by the standard hexokinase method. By comparison, the determinations made in accordance with the practice of this invention are much easier, nonenzymatic, much faster, less expensive, and just as reliable.

It will be understood that changes may be made in the details of formulation and operation without departing from the spirit of the invention, especially as defined in the following claims.

We claim:
1. A method for determination of hydrogen peroxide, sugars and other polyhydroxy compounds comprising providing the compound in an aqueous alkaline solution, applying a constant potential between a transition metal oxide catalyst electrode and a counter electrode immersed in the solution whereby electrocatalytic oxidation of the hydroxy compound occurs at the surface of the transition metal oxide electrode, and measuring the rise in current from the electrochemical oxidation.

2. The method as claimed in claim 1 in which the solution has a pH within the range of 10 to 14.

3. The method as claimed in claim 1 in which lithium hydroxide is present in the dissolved state in the solution.

4. The method as claimed in claim 1 in which the solution contains ions of the transition metal of the oxide catalyst electrode.

5. The method as claimed in claim 1 in which the oxide electrode is covered with a microporous membrane to keep proteins and high molecular weight molecules from interfering with the determination.

6. The method as claimed in claim 1 in which the solution contains the material to be determined in a concentration within the range of $1 \times 10^{-7}$ to $1 \times 10^{-2}$ M.

7. The method as claimed in claim 1 in which, when the polyhydroxy compound is serum glucose, the oxide electrode is protected with a microporous membrane and the solution has a pH within the range of 11 to 13, with lithium hydroxide and ions of the metal of the electrode present in low concentration in the solution.

8. The method as claimed in claim 1, in which, in the determination of serum triglyceride, the polyhydroxy compound is glycerol derived by hydrolyzation of the serum triglyceride to glycerol and fatty acid.

9. The method as claimed in claim 8 in which the hydrolyzation is carried out by reacting the serum triglyceride with the enzymes lipase and α-chymotrypsin.

10. The method as claimed in claim 9 in which the reaction is carried out by incubation.

11. The method as claimed in claim 1 in which, in the determination of cholesterol in blood, the polyhydroxy compound is hydrogen peroxide derived by reacting the serum cholesterol with cholesterol ester hydrolase to convert cholesterol esters to free cholesterol and reacting the free cholesterol with cholesterol oxidase to yield hydrogen peroxide.

12. The method as claimed in claim 1 in which, in the determination of sugar in urine, the urine is first reacted with urease and uricase to deactivate uric acid.

13. The method as claimed in claim 12 in which the determination of sugar in urine is made both before and after reaction of the urine with urease and uricase whereby the difference in current levels indicates the amount of sugar in the urine.

14. The method as claimed in claim 1 in which the transition metal oxide is the oxide of the metal selected from the group consisting of manganese, copper, nickel, cobalt and siver.

15. The method as claimed in claim 1 in which the current rise is compared with the current rise of a known standard solution of hydroxy compound.

* * * * *